US007972282B2

(12) United States Patent
Clark et al.

(10) Patent No.: US 7,972,282 B2
(45) Date of Patent: Jul. 5, 2011

(54) TORQUE DEVICE FOR A MEDICAL GUIDEWIRE

(75) Inventors: Timothy W. I. Clark, Philadelphia, PA (US); Greg McArthur, Sandy, UT (US); William Padilla, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 985 days.

(21) Appl. No.: 11/688,766

(22) Filed: Mar. 20, 2007

(65) Prior Publication Data

US 2007/0219467 A1      Sep. 20, 2007

Related U.S. Application Data

(60) Provisional application No. 60/783,665, filed on Mar. 20, 2006.

(51) Int. Cl.
*A61M 25/00* (2006.01)
(52) U.S. Cl. .................................................. 600/585
(58) Field of Classification Search .................. 600/585
See application file for complete search history.

(56) References Cited

U.S. PATENT DOCUMENTS

| 3,452,740 A | 7/1969 | Muller |
| 4,796,626 A | 1/1989 | DeVries |
| 4,799,496 A | 1/1989 | Hargreaves et al. .......... 128/772 |
| 4,829,999 A | 5/1989 | Auth |
| 4,858,810 A | 8/1989 | Intlekofer et al. |
| 4,860,742 A | 8/1989 | Park et al. |
| 4,957,147 A | 9/1990 | Lowe |
| 4,973,329 A | 11/1990 | Park et al. .......................... 606/1 |
| 5,137,517 A | 8/1992 | Loney et al. .................. 604/159 |
| 5,161,534 A | 11/1992 | Berthiaume .................. 128/657 |
| 5,219,332 A | 6/1993 | Nelson et al. .................. 604/95 |
| 5,312,338 A | 5/1994 | Nelson et al. .................. 604/95 |
| 5,325,746 A | 7/1994 | Anderson ....................... 81/487 |

(Continued)

FOREIGN PATENT DOCUMENTS

EP                534747            3/1993

(Continued)

OTHER PUBLICATIONS

Notification of Transmittal of the International Search Report and the Written Opinion of the International Searching Authority issued Dec. 14, 2007 in International Application No. PCT/US2007/06945.

(Continued)

*Primary Examiner* — Max Hindenburg
*Assistant Examiner* — Emily M Lloyd
(74) *Attorney, Agent, or Firm* — Stoel Rives LLP

(57) ABSTRACT

A torque device for selectively gripping a medical guidewire. The device includes a housing, an actuator slidably mounted on the housing, and a resilient member biasing the actuator. A lumen dimensioned to receive the guidewire extends through the housing and actuator. The resilient member biases the actuator from a first position in which the lumen portions are aligned, toward a second position in which the lumen portions are misaligned. The actuator may include a catch that interferes with a stop of the housing to retain the actuator within the housing. The actuator may be oblong or otherwise shaped to maintain the lumen portions in substantial alignment in a longitudinal direction. Preferably, at least a portion of the lumen is teardrop-shaped in cross-section. The housing may include circumferentially or longitudinally extending ribs defining an outer grasping surface. Frusto-conical cavities may be defined at entry and exit ends of the lumen.

23 Claims, 5 Drawing Sheets

U.S. PATENT DOCUMENTS

| | | | |
|---|---|---|---|
| 5,325,868 A | 7/1994 | Kimmelstiel | 128/772 |
| 5,392,778 A | 2/1995 | Horzewski | 128/657 |
| 5,423,331 A | 6/1995 | Wysham | 128/772 |
| 5,471,301 A | 11/1995 | Kumagai et al. | |
| 5,634,475 A | 6/1997 | Wolvek | 128/772 |
| 5,741,301 A | 4/1998 | Pagedas | |
| 5,800,447 A | 9/1998 | Wenstrom, Jr. | |
| 5,851,189 A | 12/1998 | Forber | 600/585 |
| 5,919,161 A | 7/1999 | Hill, III et al. | |
| 5,987,344 A | 11/1999 | West | |
| 6,015,428 A | 1/2000 | Pagedas | |
| 6,030,349 A | 2/2000 | Wilson et al. | 600/585 |
| 6,033,414 A | 3/2000 | Tockman et al. | 606/129 |
| 6,059,484 A | 5/2000 | Greive | 403/305 |
| 6,171,317 B1 | 1/2001 | Jackson et al. | |
| 6,371,940 B1 | 4/2002 | Valencia et al. | 604/164.13 |
| 6,394,976 B1 | 5/2002 | Winston et al. | |
| 6,533,772 B1 | 3/2003 | Sherts et al. | 606/1 |
| 6,626,917 B1 | 9/2003 | Craig | |
| 6,949,104 B2 | 9/2005 | Griffis et al. | 606/108 |
| 7,011,635 B1 | 3/2006 | Delay | 600/585 |
| 7,087,060 B2 | 8/2006 | Clark | |
| 7,144,378 B2 | 12/2006 | Arnott | 600/585 |
| 2001/0031973 A1 | 10/2001 | Nobles et al. | |
| 2003/0028203 A1 | 2/2003 | Clark | |
| 2003/0225395 A1 | 12/2003 | Griffis et al. | 604/528 |
| 2003/0229297 A1 | 12/2003 | Christensen et al. | 600/585 |
| 2004/0067099 A1 | 4/2004 | Warburton-Pitt | |
| 2004/0215108 A1 | 10/2004 | Windheuser | 600/585 |
| 2005/0070820 A1 | 3/2005 | Boutillette et al. | 600/585 |
| 2005/0096566 A1 | 5/2005 | Arnott | 600/585 |
| 2005/0235778 A1 | 10/2005 | Murphy et al. | |
| 2006/0030886 A1 | 2/2006 | Clark | |
| 2007/0142786 A1 | 6/2007 | Lampropoulos et al. | |
| 2007/0219467 A1 | 9/2007 | Clark et al. | |
| 2008/0269785 A1 | 10/2008 | Lampropoulos et al. | |
| 2009/0234295 A1 | 9/2009 | Lampropoulos et al. | |
| 2010/0057110 A1 | 3/2010 | Lampropoulos et al. | |

FOREIGN PATENT DOCUMENTS

| | | |
|---|---|---|
| WO | WO 01/41860 | 6/2001 |

OTHER PUBLICATIONS

Notification of Transmittal of the International Search Report and the Written Opinion of the International Searching Authority issued Jun. 25, 2009 in International Application No. PCT/US2009/037168.

European Search Report issued May 29, 2009 in co-pending European patent application No. 07753564.9.

Vorwerk, Konner, Schurmann, and Gunther, a Simple Trick to Facilitate Bleeding Control after Percutaneous Hemodialysis Fistula and Graft Interventions, Cardiovasc Intervent Radiol 20 (2) : 159-60 (1997).

Zaleski, Funaki, Gentile, and Garofalo, Purse-string Sutures and Miniature Tourniquet to Achieve Immediate Hemostasis of Percutaneous Grafts and Fistulas: a Simple Trick with a Twist, Am. J. Roentgenol. 175 (6) : 1643-5 (2000).

Simmons, Clark, and Rajan, The Woggle Technique: A New Method of Suture Closure of Hemodialysis Arteriovenous Grafts and Fistulae After Percutaneous Intervention, Journal of Vascular and Interventional Radiology 12(1) :S30 (2001).

Notice of Allowance issued Jan. 10, 2006 in co-pending U.S. Appl. No. 10/198,161.

Response and Amendment filed Oct. 6, 2005 in co-pending U.S. Appl. No. 10/198,161.

Office Action issued Apr. 6, 2005 in co-pending U.S. Appl. No. 10/198,161.

Office Action issued Feb. 7, 2005 in co-pending U.S. Appl. No. 10/198,161.

Preliminary Amendment filed Oct. 6, 2005 in co-pending U.S. Appl. No. 11/244,168.

Office Action issued Feb. 6, 2007 in co-pending U.S. Appl. No. 11/244,168.

Amendment filed Aug. 6, 2007 in co-pending U.S. Appl. No. 11/244,168.

Examiner Interview Summary in co-pending U.S. Appl. No. 11/244,168.

Office Action issued Oct. 18, 2007 in co-pending U.S. Appl. No. 11/244,168.

Notice of Abandonment issued Aug. 7, 2008 in co-pending U.S. Appl. No. 11/244,168.

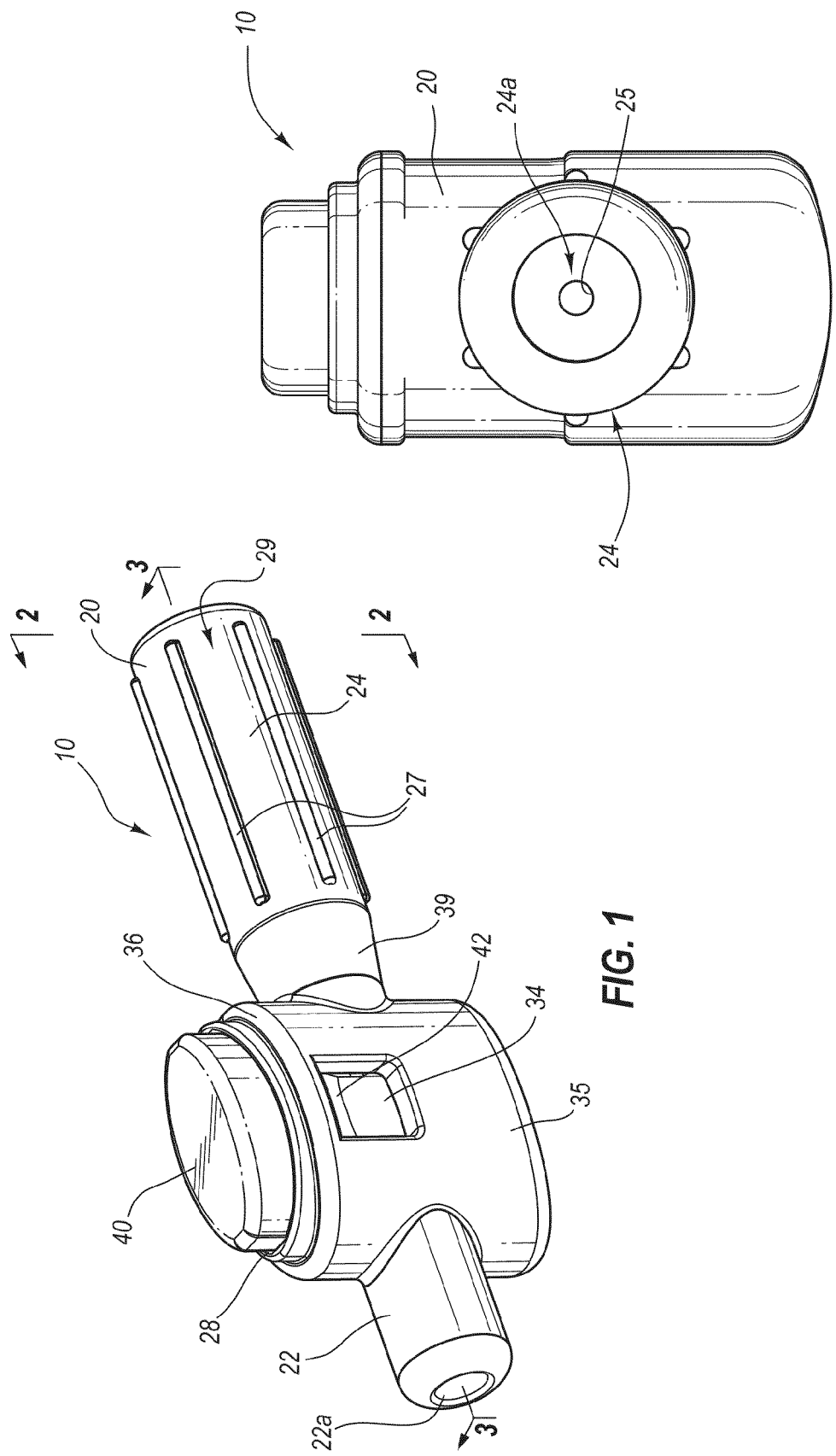

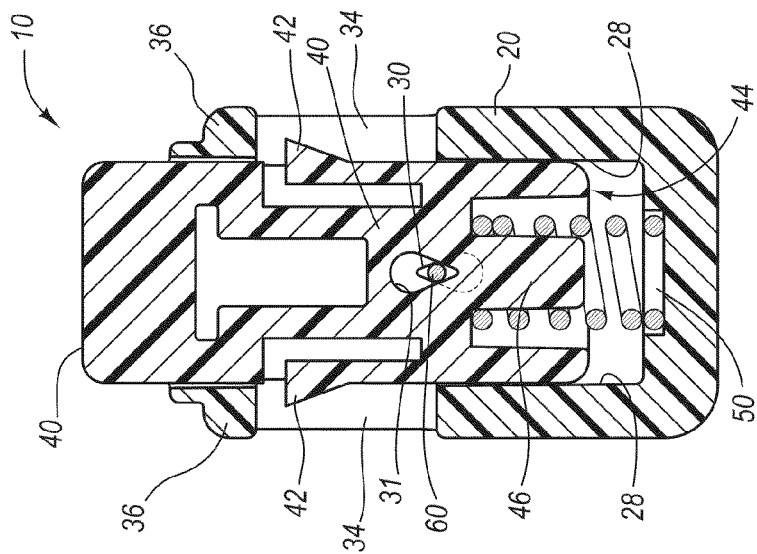
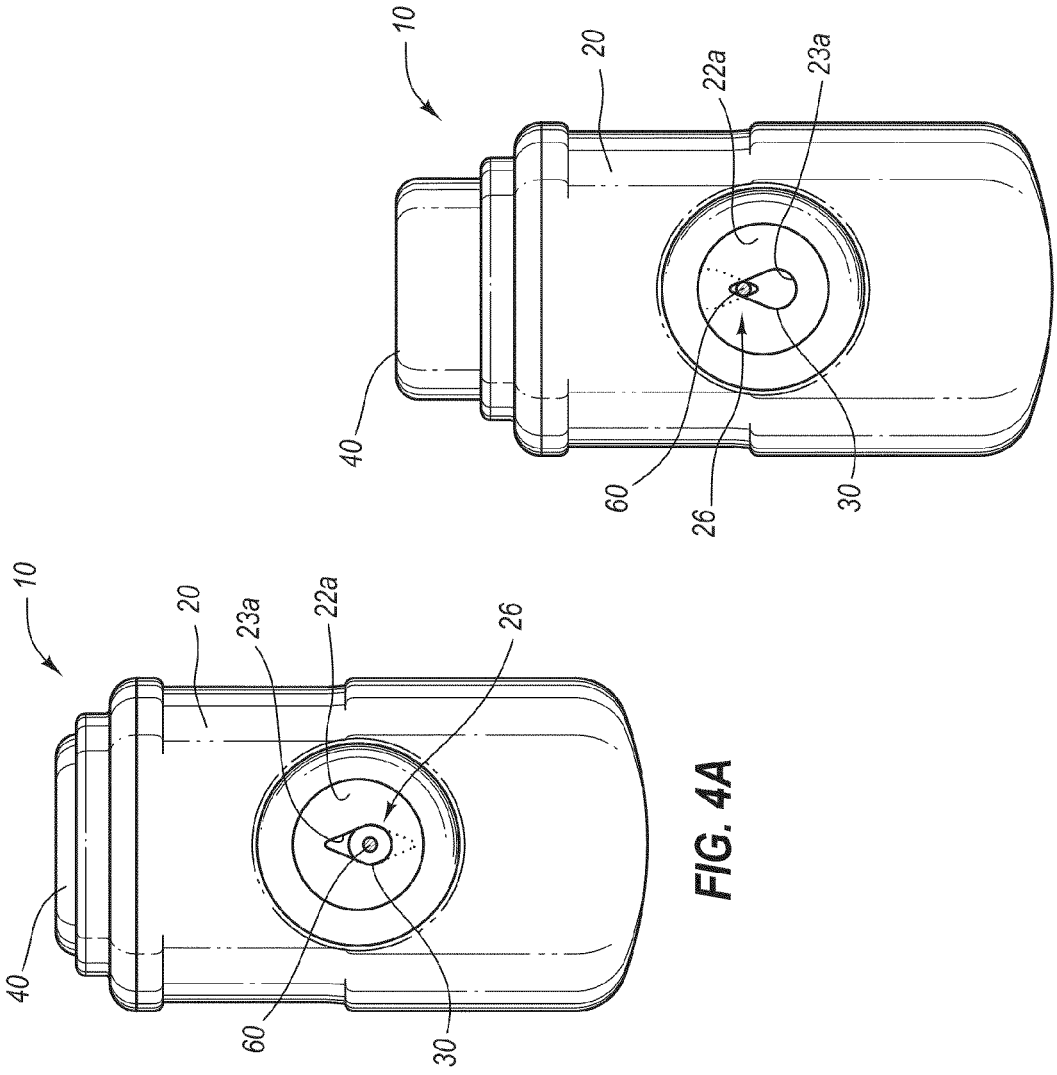

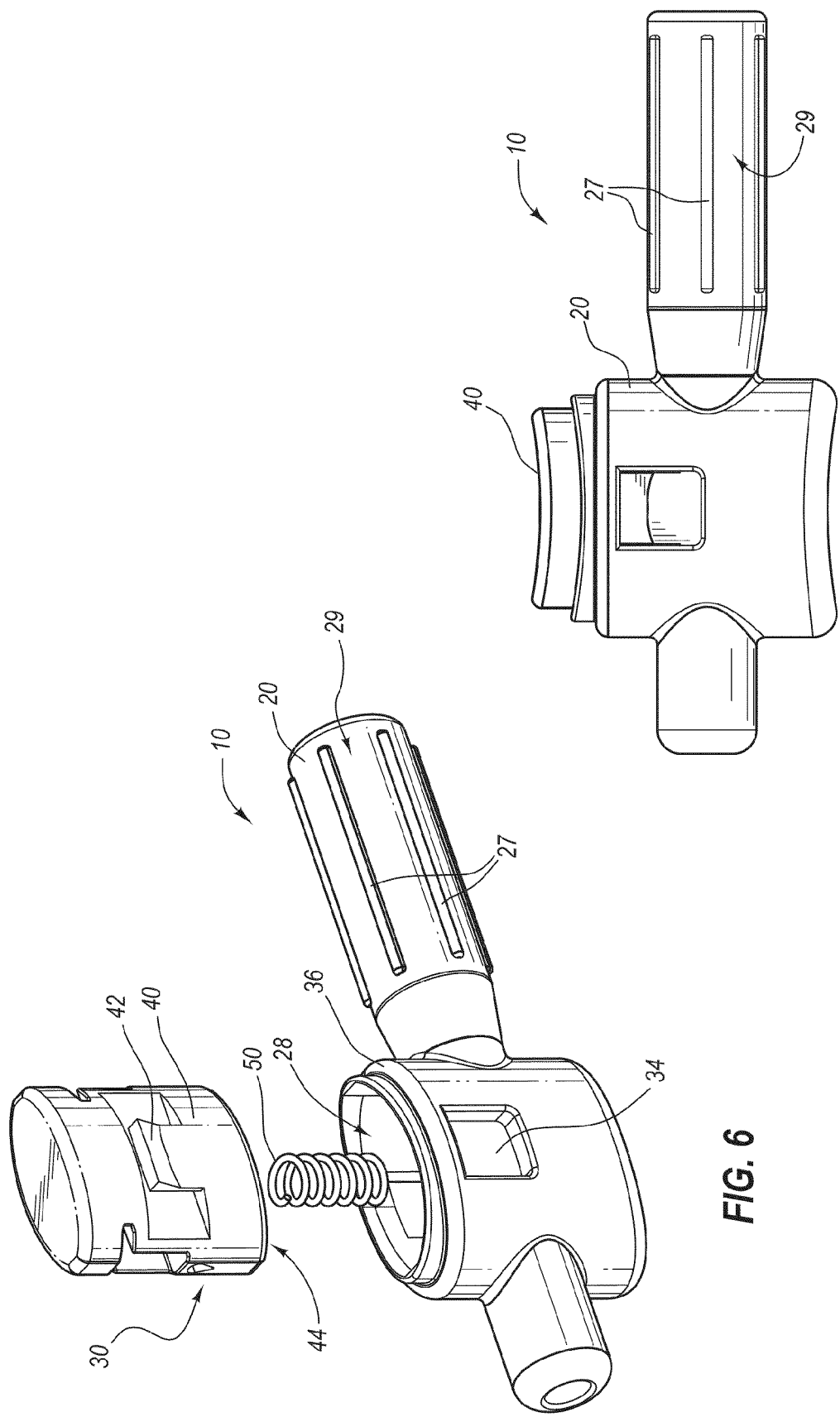

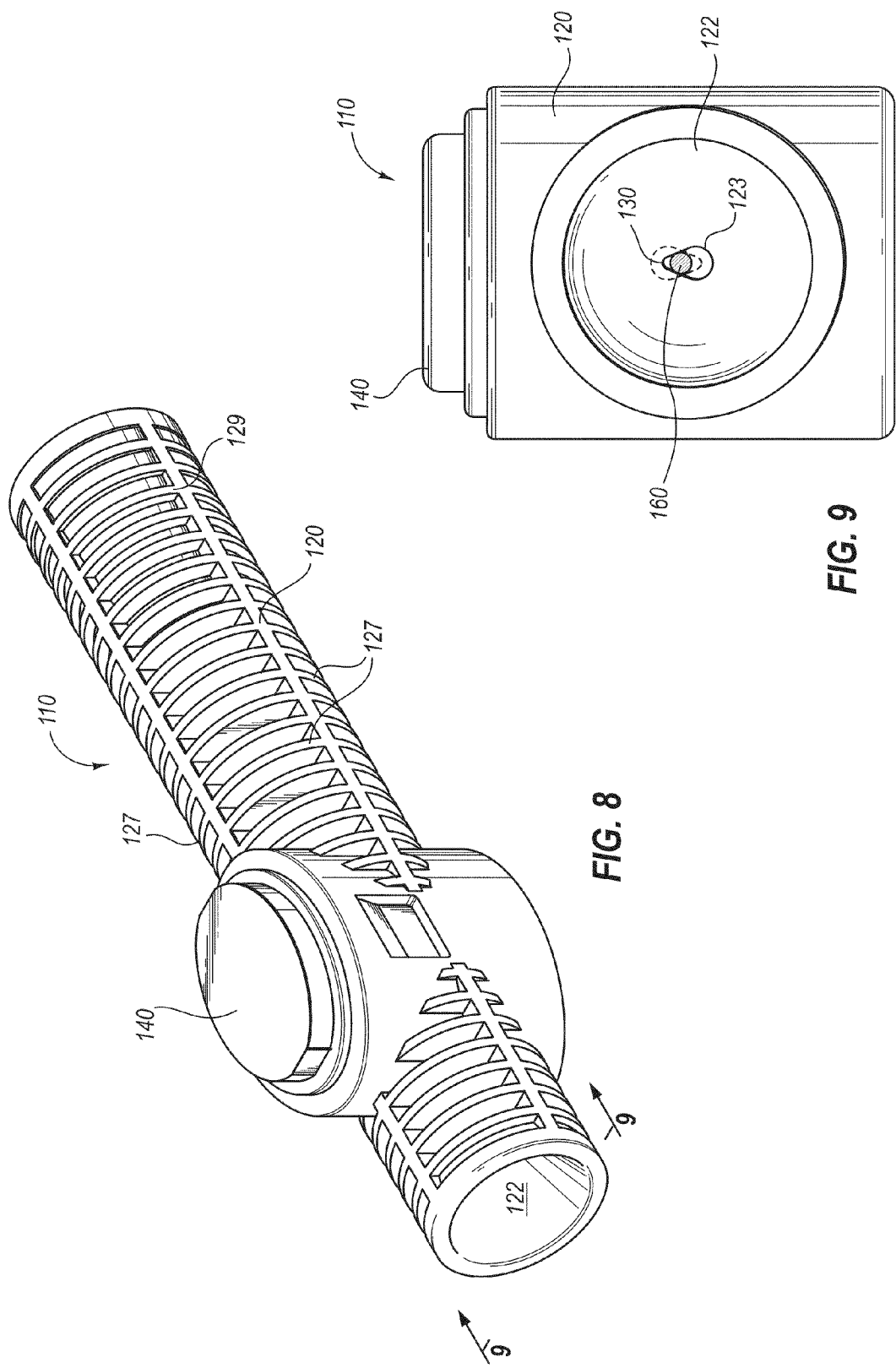

TORQUE DEVICE FOR A MEDICAL GUIDEWIRE

CROSS-REFERENCE TO RELATED APPLICATION

This application claims the benefit of U.S. Provisional Patent Application No. 60/783,665, filed Mar. 20, 2006, the entire disclosure of which is hereby incorporated herein by reference.

FIELD OF THE INVENTION

The present invention relates to a torque device configured to selectively grip a medical guidewire to facilitate maneuvering of the guidewire during an endovascular or other medical procedure.

DISCUSSION OF THE RELATED ART

Medical guidewires are commonly used for a variety of medical procedures. Such procedures include angioplasty, stenting, pacemaker insertion, electrophysiology studies, atherectomy, and thrombolysis and other coronary and peripheral endovascular procedures, and in endourology and therapeutic endoscopy of the gastrointestinal system. To position a guidewire at a desired location within a patient a medical professional navigates the guidewire through the patient's anatomy by manipulating the guidewire. Such manipulation includes advancing of the guidewire into a patient's vasculature or other portion of the patient's body while torqueing the guidewire. Torqueing the guidewire allows the medical professional to change the spatial orientation of the tip of the guidewire when negotiating turns and branches in the patient's vasculature or other relevant portion of the patient's anatomy.

To manipulate the guidewire, medical professionals have traditionally used devices which require two-handed operability. As the guidewire is advanced into the patient's artery, etc., the distance between the patient's body and the torque device decreases. When the proximity between the patient's body and the torque device decreases, the medical professional will loosen the torque device, reposition the torque device proximally along the guidewire to provide an additional length of guidewire between the patient's body and the torque device, and then tighten the torque device to secure its position along the length of the guidewire. The process of loosening and repositioning the torque device may be repeated several times during the placement of the guidewire.

Many of the commercially-available torque devices require two-handed operability to loosen and tighten the device. Due to the complexities of some guidewire placement procedures, it can be inconvenient or impractical for a practitioner to utilize both hands to thread the guidewire through the catheter or reposition the torque device along the length of the guidewire. As a result, additional care and attention are required when manipulating the torque device relative to the guidewire during the procedure. This can lengthen the amount of time and the degree of difficulty necessary to complete the guidewire placement procedure. Additionally, traditional devices are often not adequately intuitive leading to misuse of the device and inadvertent damage to the guidewire. These devices can require specialized training to facilitate proper usage of the device and can still result in inadvertent misuse of the device during the course of the procedure. Additionally, some devices do not provide adequate gripping of the guidewire as may be required to push the guidewire through a vascular lesion or other guidewire path occlusion. Where an occlusion is encountered, the practitioner may over tighten the device in a manner that causes damage to the guidewire.

SUMMARY OF THE INVENTION

The present invention is directed to a torque device for a medical guidewire that allows for one-handed operability, improved gripping, and which avoids improper usage and/or damage to the guidewire. According to one embodiment of the present invention, the torque device includes a button which is configured to allow for securement of the guidewire when the button is released and allowing movement of guidewire relative to the torque device when the button is depressed. In one configuration, the button is spring-biased to a configuration in which the torque device securely embraces the guidewire.

The torque device includes a housing, a slidable actuator and a resilient biasing member. The housing defines a first and third portion of a lumen dimensioned to receive the guidewire. The slidable actuator defines a second portion of the lumen. The resilient member biases the actuator from a first position in which the first and second portions of the lumen and second and third portions of the lumen are aligned, toward a second position in which the first and second portions of the lumen are misaligned and the second and third portions of the lumen are misaligned. The lumen can be substantially continuous through the housing and actuator. According to one embodiment of the present invention, when the actuator is in the second position, the guidewire is effectively secured allowing for gripping of the guidewire, advancing of the guidewire into the patient, or torqueing the guidewire to change the spatial orientation of the end of the guidewire. When the actuator is in the first position, the torque device can be positioned or repositioned along the length of the guidewire.

According to one illustrative embodiment of the present invention, the lumen has a tear drop, triangle, elliptical or other non-circular shape which provides at least two elongated areas of contact between the guidewire and the lumen which can facilitate gripping of the guidewire. The non-circular shape can also facilitate desired gripping of guidewires of varying diameters. According to another illustrative embodiment of the present invention, first and second portions of the lumen have a non-circular cross-section which are inverted relative to one another. For example, the lumen of the housing is shaped like a tear drop in a normal tear drop orientation with the point of the tear drop at the top of the lumen. The lumen of the actuator is also shaped like a tear drop with the point of the tear drop being placed at the bottom of the lumen. When the actuator is released such that the guidewire is secured, the inverted tear drop shape of the opposing actuator lumen and the housing lumen cooperatively engage the guidewire providing four points of engagement on the guidewire.

According to one embodiment of the present invention, proper usage of the torque device is intuitive, substantially decreasing the likelihood of misuse of the device and/or inadvertent damage to the guidewire with which the torque device is utilized. For example, when the actuator button of the torque device is depressed, the lumens of the first and second portion of the torque device are aligned in a manner that facilitates insertion of the guidewire through the torque device from either end of the torque device. When the actuator button is released, the guidewire is automatically engaged at desired levels of gripping minimizing the risk of kinking or other damage to the guidewire. Additionally, the configuration of the actuator button makes it difficult or impractical for the medical professional to exert a higher degree of gripping forces on the guidewire that could lead to kinking or damage to the guidewire.

A portion of the housing may define a stop, and the actuator may include a catch, such that movement of the actuator in a direction of the bias is limited by interference of the catch with the stop. For example, the housing may define a stop adjacent to an opening of the housing and the actuator may define a resilient catch. The resilient catch can be configured to deflect during assembly of the actuator to the housing. During assembly as the catch abuts the stop the catch will bias inward allowing the catch to pass the stop and enter the opening. According to one embodiment of the present invention, the resilient catch allows for quick and advantageous snap-assembly of the torque device, reducing the cost of manufacture of the device.

The housing and actuator may be shaped to maintain the first and second portions of the lumen in substantial alignment in a longitudinal direction of the device.

BRIEF DESCRIPTION OF THE DRAWINGS

The present invention will now be described by way of example with reference to the following drawings in which:

FIG. 1 is a perspective view of a torque device according to an exemplary embodiment of the present invention;

FIG. 2 is an end view of the torque device of FIG. 1;

FIG. 4A is an end view of the torque device of FIG. 1 in which the actuator of the torque device is depressed allowing movement of a guidewire relative to the torque device;

FIG. 4B is an end view of the torque device of FIG. 1 in which the actuator of the torque device is released securing the position of the torque device relative to the guidewire;

FIG. 5 is a cross-sectional view of the torque device of FIG. 1;

FIG. 6 is an exploded perspective view of the torque device of FIG. 1;

FIG. 7 is a side view of the torque device of FIG. 1;

FIG. 8 is a perspective view of an exemplary embodiment of the torque device according to an exemplary embodiment of the present invention; and FIG. 9 is an end view of the torque device of FIG. 8.

DETAILED DESCRIPTION

Figure 3A:
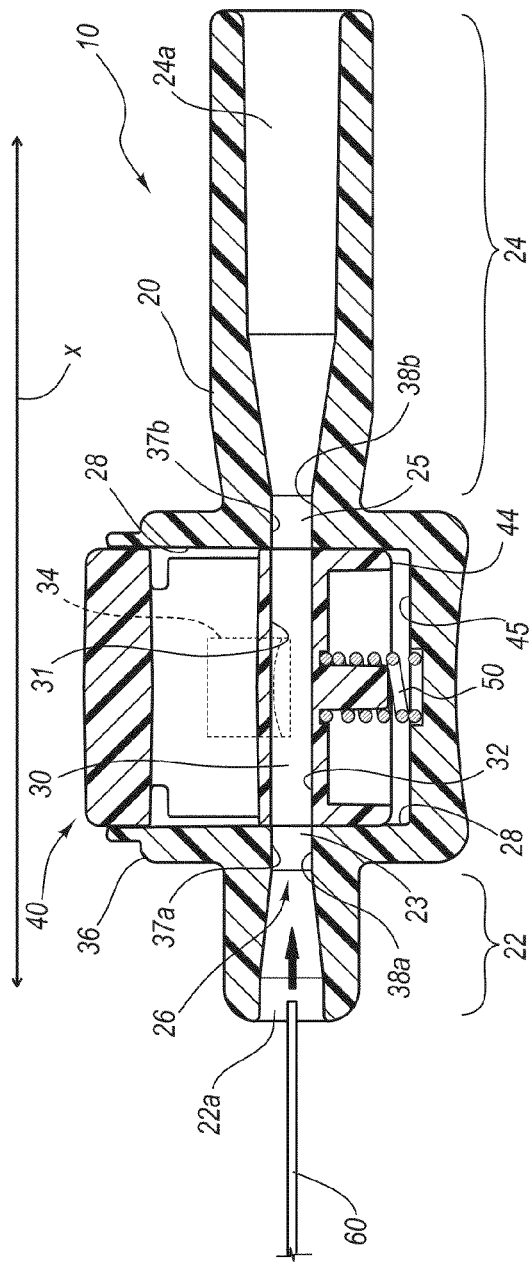
FIG. 3A is a cross-sectional view of the torque device of claim 1, taken along line 3-3 of FIG. 1 in which an actuator of the torque device is depressed.

The present invention is directed to a torque device 10 configured to selectively grip a medical guidewire 60 and to permit torqueing of the guidewire by manipulation of the torque device 10. Torque device 10 provides one-handed and intuitive operability facilitating ease of use and reducing the likelihood of misuse of torque device 10 that could result in damage to guidewire 60. According to one embodiment of the present invention, torque device 10 comprises a push-to-release configuration in which the device is automatically spring-biased to a position in which the torque device securely grips the guidewire when an actuator 40 of torque device 10 is not depressed. According to another embodiment of the present invention, torque device 10 can be manufactured utilizing three components and is thus reliable and simple to manufacture.

FIG. 1 is a perspective view of a torque device 10 according to one embodiment of the present invention. Torque device 10 is configured to selectively grip a guidewire to facilitate manipulating of the guidewire during a guidewire insertion procedure. In the illustrated embodiment, torque device 10 comprises a housing 20 and an actuator 40.

In the illustrated embodiment, housing 20 provides a foundation for securement of the other components of torque device 10. According to one embodiment of the present invention, housing 20 is formed as a unitary body, as by injection molding of a polycarbonate material or similar material. Housing 20 comprises a body 35, a distal end 22, a proximal end 24 and a channel 28. Body 35 comprises a barrel member to which the other components of housing are secured. Distal end 22 is integrally secured to the body 35 between body 35 and the patient. Distal end 22 provides a channel which allows for introduction of a guidewire into torque device 10. Proximal end 24 is integrally secured to body 35 opposite distal end 22. Proximal end 24 comprises a handle which allows a practitioner to grasp torque device 10 to hold and manipulate torque device 10 as required during the procedure being performed. Proximal end 24 also provides a channel which allows for introduction of a guidewire into torque device 10. Channel 28 is defined by body 35. Channel 28 is configured to accommodate actuator 40 and to allow for desired movement of actuator 40 within channel 28. In the illustrated embodiment, channel 28 provides a uniform sliding surface which allows for desired movement of actuator 40 when a practitioner depresses actuator 40 during operation of torque device 10. Optionally, a lower portion of housing 20 may be shaped to provide a concave surface to provide an ergonomic gripping surface.

In the illustrated embodiment, a cavity 22a having a frusto-conical surface is provided in connection with distal end 22. Cavity 22a is adapted to facilitate insertion of a guidewire into torque device 10. The tapered configuration of the frusto-conical surface of cavity 22a allows for a wider opening into which an end of a guidewire can be inserted. Once the guidewire has been inserted into the cavity 22a, the frusto-conical surface of cavity 22a will direct the tip of the catheter to the more narrow guidewire lumen of the torque device. In the illustrated embodiment, proximal end 24 also includes a cavity 24a (see FIG. 2) having a frusto-conical surface facilitating insertion of guidewire into proximal end 24.

Proximal end 24 includes ribs 27, an outer grasping surface 29 and a tapered section 39. Outer grasping surface 29 is specially-configured to enhance tactile grip. According to the illustrated embodiment of the present invention, outer grasping surface 29 is substantially cylindrical in overall shape, e.g., in transverse cross-section.

Ribs 27 comprise a plurality of longitudinally extending members which provide an ergonomic grasping surface in connection with outer grasping surface 29. The configuration of ribs 27 provides a relief surface on the exterior of proximal end 24 which facilitates grasping of proximal end 24. The combination of the shape of grasping surface 29 and the ribs 27 are believed to facilitate manual grasping and manipulation of the device by the medical professional. Tapered section 39 is positioned at the portion of proximal end 24 adjacent body 35. Tapered section 39 facilitates grasping of proximal end 24 when exerting a tensile force on a guidewire. In this manner, the practitioner can firmly grip proximal end 24 when withdrawing a guidewire from a patient.

In the illustrated embodiment, actuator 40 is positioned within channel 28 of housing 20. According to one embodiment of the present invention, actuator 40 is formed as a unitary body, as by injection molding of a polycarbonate material. Actuator 40 allows the practitioner to engage or release a guidewire being utilized in connection with torque device 10. When actuator 40 is in a first position, torque device 10 can be positioned or repositioned along the length of a guidewire. When actuator 40 is in a second position, the guidewire can be effectively secured allowing for gripping of the guidewire, advancing of the guidewire into the patient, or torqueing the guidewire to change the spatial orientation of an end of the guidewire.

In the illustrated embodiment, the practitioner can depress actuator 40 to release a guidewire allowing for movement of a guidewire relative to torque device 10. When actuator 40 is released the guidewire is secured minimizing movement of the guidewire relative to torque device 10. In the illustrated embodiment actuator 40 comprises a button. Proper usage of torque device 10 is configured to be intuitive; substantially decreasing the likelihood of misuse of torque device 10 and/or inadvertent damage to a guidewire with which torque device 10 is utilized. For example, when actuator 40 is depressed a guidewire can be inserted through torque device 10 from either distal end 22 or proximal end 24 of the torque device. Additionally, the configuration of actuator 40 minimizes the ability of a practitioner to exert forces on the guidewire that exceed the desired amount of force that is automatically exerted on the guidewire when actuator 40 is not depressed.

When actuator 40 is released, a guidewire being utilized with torque device 10 is engaged. In the illustrated embodiment, actuator 40 includes catch 42 while body 35 of housing 20 includes an opening 34 and a stop 36. Catch 42 moves within opening 34 during depression and release of actuator 40. Stop 36 minimizes upward (as shown in the Figures) movement of actuator 40 to maintain actuator within housing 20. As a result, when actuator 40 is released the guidewire is automatically engaged at desired levels of gripping thus minimizing the risk of kinking or other damage to the guidewire. Additionally, the interaction between stop 36 and catch 42 makes it difficult and/or impractical for the medical professional to exert a higher degree of gripping forces on the guidewire in a manner that could damage the guidewire.

FIG. 2 is an end view of torque device 10 according to one embodiment of the present invention. In the illustrated embodiment, a proximal portion 25 of a lumen that extends longitudinally along the length of torque device 10 is illustrated. When a practitioner inserts a guidewire into torque device 10 through proximal end 24, the guidewire is directed for insertion into proximal portion 25. In the illustrated embodiment, a cavity 24a having a frusto-conical surface is provided in connection with proximal end 24 facilitating insertion of a guidewire into proximal portion 25. The tapered configuration of the frusto-conical surface of cavity 24a allows for a wider opening in which an end of a guidewire can be inserted. Once the guidewire has been inserted into the cavity 24a, the frusto-conical surface will direct the tip of the catheter to the relatively narrower opening of proximal portion 25 of the guidewire lumen.

Figure 3B:
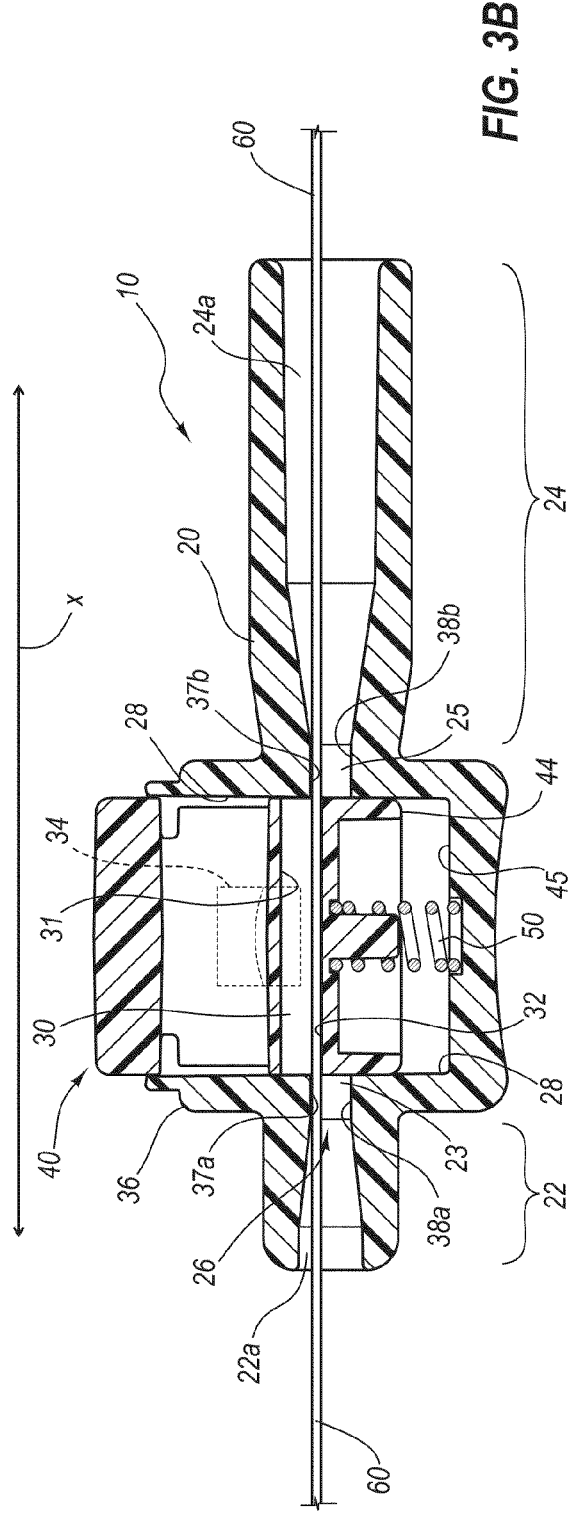
FIG. 3B is a cross-sectional view of the torque device of FIG. 1, in which the actuator of the torque device is released.

FIGS. 3A and 3B illustrate cross-sectional side views of torque device 10 of FIG. 1 taken along lines 3-3 of FIG. 1. In the illustrated embodiment, housing 20 is elongated in the longitudinal direction X and has a distal end 22 and a proximal end 24. A guidewire lumen 26 is provided which permits passage of guidewire 60 through the length of torque device 10. Guidewire lumen 26 is dimensioned to receive one or more diameters of guidewire 60. Actuator 40 defines a longitudinally-extending actuator portion 30 of the lumen 26. Distal end 22 defines a distal portion 23 of guidewire lumen 26. Proximal end 24 defines a proximal portion 25 of guidewire lumen 26. The combination of distal portion 23, actuator portion 30 and proximal portion 25 provides a configuration of lumen 26 which extends longitudinally through torque device 10.

With reference first to FIG. 3A, channel 28 extends linearly and substantially perpendicularly to a direction of elongation X of the lumen 26. The actuator 40 is mounted in the channel 28 for sliding motion in a linear direction Y that is substantially perpendicular to the direction of elongation X of the lumen 26. When actuator 40 is depressed, lumen 26 is substantially continuous through the housing 20 and the actuator 40. In other words, when the actuator 40 is depressed to align the actuator portion 30 of the lumen 26 with the proximal and distal portions 25, 23 of the lumen 26, the lumen 26 has a sidewall that is longitudinally continuous except for potential air gaps between the actuator 40 and the housing 20 adjacent the proximal and distal ends of the actuator portion 30 of the lumen 26. Thus, the lumen 26 is substantially continuous from the distal portion 23, through the actuator portion 30, to the proximal portion 25.

In the illustrated embodiment, actuator 40 is depressed such that distal portion 23, proximal portion 25 and actuator portion 30 of the lumen 26 are longitudinally-aligned to permit passing of guidewire 60 through torque device 10. In the illustrated embodiment, actuator 40 includes a stop surface 44 on the bottom of actuator 40. When actuator 40 is fully depressed, stop surface 44 contacts channel floor 45. When stop surface 44 is in contact with channel floor 45, actuator portion 30 is aligned with distal and proximal portions 23 and 25. In other words, in order to align actuator portion 30 with proximal and distal portions 23, 25 and allow passage of guidewire 60 through lumen 26 of torque device 10 the practitioner simply depresses actuator 40 until the practitioner can no longer displace actuator 40 in a downward direction (as shown in the Figures). This provides a simple, intuitive and straightforward operation of torque device 10.

With reference now to FIG. 3B, in the illustrated embodiment guidewire 60 has been threaded along the entire length of torque device 10. Actuator 40 has been released such that a resilient biasing member 50 has biased actuator 40 to a released/non-depressed position. Stop surface 44 of actuator 40 is no longer in contact with channel floor 45 and actuator portion 30 of lumen 26 is no longer aligned with proximal and distal portions 23, 25 of lumen 26.

Actuator portion 30 of lumen 26 includes an upper wall surface 31 and a lower wall surface 32. Upper wall surface 31 is continuous with lower wall surface 32 through the actuator portion 30. Distal portion 23 of lumen 26 includes an upper wall surface 37a and a lower wall surface 38b. Proximal portion 25 of lumen 26 also includes an upper wall surface 37b and a lower wall surface 38b. When actuator 40 is released as depicted in FIG. 3B, guidewire 60 is cooperatively engaged between lower wall surface 32 and upper wall surfaces 37a, 37b. The cooperative engagement of guidewire 60 between lower wall surface 32 and upper wall surfaces 37a, 37b cooperatively grips guidewire 60 to maintain the position of torque device 10 along the length of guidewire 60.

Channel 28 and actuator 40 are configured to prevent rotation of the actuator 40 about an axis that extends in a direction Y perpendicular to a direction of elongation X of the lumen to maintain substantial longitudinal alignment of the actuator portion 30 of the lumen with the proximal and distal portions 23, 25 of the lumen 26. The perpendicular movement of actuator 40 relative to housing 20 and lumen 26 allows for closer tolerances between portions of lumen 26 associated with actuator 40 and housing 20. As a result, bending of guidewire 60 is minimized due to the interactions of housing 20 and actuator 40 when guidewire is engaged.

In the illustrated embodiment, lumen 26 has a substantially continuous configuration. In other words, actuator 40 provides an increased area of contact between actuator 40 and guidewire 60 to minimize bending or kinking of guidewire 60. Additionally, distal and proximal portions 23 and 25 provide a somewhat elongated contact area between housing 20 and guidewire 60. As compared with designs having only discrete points of contact, this arrangement minimizes bending or kinking of the guidewire 60. Additionally, contact between guidewire 60, actuator portion 30, distal portion 23 and proximal portion 25 facilitates desired gripping of guidewire 60. This, in turn, results in the ability to use a resilient member/spring having a lower spring force to provide the amount of friction required to permit torqueing of the guidewire by torqueing of the device. The lesser spring force results in greater ease of operation of the actuator, less manual fatigue of the medical professional, and less risk of damage to the guidewire due to kinking, etc.

In the event that a guidewire has not been inserted into torque device 10 and where actuator 40 is not depressed, the resulting lack of alignment between actuator portion 30 and proximal and distal portions 23, 25 will prevent passage of a guidewire through torque device 10. In the event that a practitioner attempts to insert guidewire 60 into torque device 10 without first depressing actuator 40, the intuitive nature and operability of torque device 10 will typically result in depression of the actuator 40 by the practitioner when the practitioner recognizes that the guidewire 60 is encountering resistance. In other words, the simple design and straight forward operability of torque device 10 allows practitioners and other medical professionals to load and operate torque device 10 without specialized training and with minimized risk of damage to guidewire 60.

FIGS. 4A and 4B illustrate an end view of torque device 10 according to one embodiment of the present invention. In the illustrated embodiment, distal portion 23a and actuator portion 30 have a non-circular tear drop shape in transverse cross-section. The non-circular tear drop shape of lumen portions 23a and actuator portions 30 facilitates optimized gripping of guidewire 60 by lumen 26. The non-circular shape of lumen portion 23a and actuator portion 30 can also facilitate desired gripping of guidewires of varying diameters.

In the illustrated embodiment, the shape of the transverse cross-section of distal portion 23a and actuator portion 30 have non-circular shapes which are inverted relative to one another. For example, distal portion 23a of lumen 26 is shaped like a tear drop with the point of the tear drop being positioned at the top of the distal portion 23a of lumen 26. The actuator portion 30 is also shaped like a tear drop with the point of the tear drop being positioned at the bottom of the actuator portion 30 of lumen 26. As will be appreciated by those skilled in the art a variety of orientations of non-circular transverse cross-sections can be utilized without departing from the scope and spirit of the present invention.

With reference now to FIG. 4A, when actuator 40 is depressed the larger cross-sectional areas of the non-circular portions of distal portion 23a and actuator portion 30 are aligned allowing for clearance between the guidewire 60 and the wall of lumen 26. As a result, guidewire 60 can be moved within lumen 26 allowing for threading of guidewire 60 through torque device 10 or repositioning of torque device 10 along the length of guidewire 60.

With reference now to FIG. 4B, when actuator 40 is released, the more narrow cross-sectional areas of the non-circular portions of distal portion 23a and actuator portion 30 contact guidewire 60. The upper wall surface of distal portion 23a contacts guidewire 60 at two points on the upper surface of guidewire 60. The lower wall surface of actuator portion 30 contacts the lower surface of guidewire 60. In this manner, guidewire 60 is sandwiched between actuator portion 30 and distal portion 23a with a total of four elongated areas of contact between actuator portion 30 and distal portion 23a. Additionally, four elongated areas of contact will be provided at the interface of actuator portion 30 and proximal portion 25 (see FIG. 3B). Furthermore, contact can be provided along the length of distal portion 23a, actuator portion 30 and proximal portion 25 as depicted with reference to FIG. 3B. As a result, optimized securement of guidewire is provided without exerting excessive forces on any one contact area along the length of guidewire. According to one embodiment of the present invention, where the shape of the teardrop results in an angle of less than 120 degrees, the spring force which provides for securement between the teardrop surfaces of the lumen and the guidewire is multiplied, providing for a mechanical advantage for gripping of the guidewire.

The tapered configuration of the teardrops allows for effective securement of a variety of diameters of guidewires. For example, where a smaller guidewire is utilized, the guidewire will be engaged closer to the narrow point of the teardrop cross-sections of actuator portion 30 and distal portion 23a (see FIG. 4B). Where a larger diameter guidewire is utilized, the guidewire will be engaged further from the narrow points of the teardrop cross-sections (see FIG. 9). As a result, four elongated areas of contact and a similar overall contact area are provided by lumen 26 notwithstanding the size of the catheter being utilized. According to one embodiment of the present invention, a single size of torque device 10 is configured to be utilized with guidewires in a range of between 0.010" and 0.038" in diameter. In another embodiment, a single size of lumen of torque device 10 is provided which can secure guidewires having a range of between 0.014" and 0.034" in diameter. In another embodiment, a single size of lumen of torque device 10 is provided which can secure catheters having a range of between 0.018" and 0.028" in diameter.

As will be appreciated by those skilled in the art, a variety of non-circular lumen cross sections can be utilized including one or more combinations of tear drop, triangle, elliptical or other non-circular shape. According to one embodiment of the present invention the actuator portion of the lumen is circular in transverse cross-section and the proximal and distal portions of the lumen are teardrop-shaped in cross-section. These arrangements facilitate secure gripping of the guidewire, as discussed in greater detail below. According to another embodiment of the present invention, the actuator portion of the lumen has a triangular configuration and the proximal and distal portions of the lumen are circular or oval in transverse cross section.

According to one embodiment of the present invention, the material properties of one or more components of the torque device are designed to facilitate gripping of the guidewire. For example, according to one embodiment of the present invention the housing, the actuator, and/or one or more portions of the lumen are comprised of polypropylene, polyethylene, acetyl reins such as Delrin®, a combination of the aforementioned, or materials having similar shore properties. According to another embodiment of the present invention the material properties of the housing and the actuator are different from one another.

FIG. 5 is a cross-sectional view of torque device 10 according to one embodiment of the present invention. In the illustrated embodiment, the juxtaposition of housing 20, actuator 40 and resilient biasing member 50 is depicted. Housing 20 defines a stop 36 and the actuator 40 defines a catch 42, such that movement of actuator 40 is limited by interference of catch 42 with stop 36. A resilient tang is one example of a catch 42. As will be appreciated by those skilled in the art, any suitable structures may be used to provide a stop and catch. In the exemplary embodiments, housing 20 defines opening 34, and stop 36 is defined by a portion of the housing 20 adjacent opening 34. Further, the actuator's 40 catch is provided as a resilient catch 42 that is received in the opening 34 and that interferes with the housing's stop 36 to retain the actuator 40 within the channel 28.

As previously discussed, actuator 40 defines a stop surface 44. As previously discussed, stop surface 44 is positioned to prevent actuator travel within the channel 28 during depression of the actuator 40 beyond a point at which the distal and proximal portions 23, 25 of the lumen 26 are longitudinally aligned with the actuator portion 30. According to one embodiment of the present invention, the forces exerted by a resilient member on the actuator are predetermined to reduce the likelihood of damage to the guidewire. Optionally, catches 42 and openings 34 can be configured to limit upward travel of the actuator 40 within the channel 28 during release of the actuator 40 to reduce the likelihood of damage to the guidewire due to shear forces applied to the guidewire by the actuator 40 and housing 20.

The device 10 further includes a resilient member which biases the actuator 40 toward a position in which the actuator portion 30 of the lumen 26 is misaligned with the proximal and distal portions 23, 25 of the lumen defined by the housing 20. As will be appreciated by those skilled in the art, the resilient member may be any resilient body capable of providing resilient bias to the actuator. In the exemplary embodiments, the resilient member is a coil spring 50. In the illustrated embodiment in which the resilient member comprises coil spring 50, actuator 40 includes a post 46 dimensioned to receive and support the coil spring 50.

FIG. 6 is a component view of torque device 10 according to one embodiment of the present invention. The configuration of torque device 10 provides for simple and efficient assembly of torque device 10. For example, torque device 10 can be assembled by inverting the actuator 40, placing the coil spring 50 over the post 46 (see FIG. 5) of the actuator 40, and placing the inverted housing 20 over actuator 40. Actuator 40 and housing 20 may then be squeezed together until the resilient catches 42 deflect inwardly as they ride against the stops 36 of the housing, and then bias in an outward direction as they clear the stops 36 of the housing and enter the openings 34 in the housing 20. Subsequent to insertion of actuator 40 within channel 28, torque device 10 is a self-maintaining, integral assembly. In other words, actuator 40 will not be ejected by spring 50 if released, but instead will be retained within housing 20 due to interference of catches 42 with stops 36.

FIG. 7 is a side perspective view of torque device 10 according to one embodiment of the present invention. In the illustrated embodiment, an upper portion of actuator 40 is shaped to provide a concave surface to provide an ergonomic gripping surface. In use in a medical procedure, actuator 40 of torque device 10 can be depressed, by a one or more fingers or a thumb, until the relevant portions of lumen 26 (see FIGS. 3A and 3B) are aligned allowing torque device 10 to be threaded onto a guidewire 60 by passing the guidewire through the lumen 26 (see FIGS. 3A and 3B). The stop surface 44 (see FIG. 5) of the actuator 40 serves to ensure that the lumen portions are properly aligned at the limit of travel of the actuator to permit free passage of guidewire through the lumen.

When the actuator 40 is released, the spring 50 biases (see FIG. 5) actuator 40 in an upward direction until the guidewire is trapped between the portions of lumen associated with the actuator and the body. The non-circular cross-sections of the portions of the lumen assist in accommodating and securely gripping guidewires of a range of gauges, sizes or diameters as discussed with respect to FIGS. 4A and 4B. The actuator 40 may be selectively depressed and released to allow for repositioning of the device 10 along the guidewire and to allow for removal of the device 10 from the guidewire, etc. during the medical procedure. The device 10 remains as an intact assembly even after removal from a guidewire, e.g. while threading a catheter onto the guidewire.

Further still, the device is provided with a specially-configured housing and actuator that limit or eliminate rotation of the actuator about an axis perpendicular to the guidewire channel, thus maintaining alignment between a section of the channel within the housing and a section of the channel within the actuator. This also reduces or eliminates binding of and/or damage to the guidewire.

Further still, the device is specially configured as a complete, operable assembly that does not rely upon the guidewire as a structural member required to maintain the alignment of components of the device, operability or structural integrity of the assembly. Accordingly, the device remains a self-contained operable assembly after removal from a first guidewire, e.g. to allow for substitution of catheters onto the guidewire during a single medical procedure.

FIG. 8 is a perspective view of a torque device 110 according to an alternative embodiment of the present invention. In the illustrated embodiment, torque device includes a housing 120 and an actuator 140. Housing is a single molded piece having a handle 129 having a plurality of gripping surfaces 127. A tapered surface 122 is provided in the proximal end of the torque device facilitating insertion of a guidewire along the length of the torque device. In the illustrated embodiment, housing 120 can be molded as a single member and actuator 140 is secured within housing by engagement of actuator 140 with one or more internal components associated with housing 120.

FIG. 9 is an end view of torque device 110 of FIG. 8. In the illustrated embodiment the non-circular cross sections of lumen portions 123 and 130 are utilized to cooperatively engage a large diameter guidewire. The upper wall surface of lumen portion 123 contacts guidewire 160 at two elongated areas on the upper surface of guidewire 160. The lower wall surface of lumen portion 130 contacts the lower surface of guidewire 160. In this manner, guidewire 160 is sandwiched between lumen portion 130 and lumen portion 123 with a minimum of four elongated areas of contact between lumen portion 130 and lumen portion 123.

The tapered configuration of the non-circular cross-section of lumen portions 123 and 130 allows for effective securement of a variety of diameters of guidewires. For example, where a smaller guidewire is utilized, the guidewire will be engaged closer to the narrow points of the teardrop cross-sections of portions 130 and 123 (see FIG. 4B). Where a larger diameter guidewire, such as guidewire 160, is utilized, the guidewire will be engaged further from the narrow points of the cross-sections. As a result, four elongated areas of contact and a similar overall contact area are provided notwithstanding the differential in size of the guidewire being utilized.

While there have been described herein the principles of the invention, it is to be understood by those skilled in the art that this description is made only by way of example and not as a limitation to the scope of the invention. Accordingly, it is intended by the appended claims, to cover all modifications of the invention which fall within the true spirit and scope of the invention.

We claim:

1. A torque device configured to accommodate a guidewire that is to be inserted into the vasculature or other physiological location of a patient, the torque device configured to engage a guidewire when the guidewire is positioned within the vasculature of the patient in a manner that a practitioner can manipulate the guidewire with a single hand by grasping and manipulating the torque device, the torque device comprising:
   a housing having an outer periphery and including a lumen which is configured to allow passage of guidewires of varying diameters,
   an actuator operably connected to the housing, the actuator having a lumen configured to allow for selective engagement of the guidewire, such that when the actuator is in a first position, the guidewire is secured relative to the torque device and when the actuator is in a second position the guidewire can be moved relative to the torque device,
   wherein the lumen of the housing and the lumen of the actuator are non-circular with a transverse cross-section having a large area that tapers to a narrow area, such that the non-circular lumen of the actuator engages the guidewire at two or more elongate areas extending along a length of the surface of the guidewire and the non-circular lumen of the housing engages the guidewire at two or more elongate areas extending along a length of the surface of the guidewire when the actuator is in the first position, wherein the transverse cross-section of the lumen of the actuator has an inverted orientation relative to the transverse cross-section of the lumen of the housing.

2. The torque device of claim 1, wherein the non-circular lumen of the actuator has a tear drop shape.

3. The torque device of claim 1, wherein the non-circular lumen of the actuator has a triangular shape.

4. The torque device of claim 1, wherein the non-circular lumen of the housing has a tear drop shape.

5. The torque device of claim 1, wherein the non-circular lumen of the housing has a triangular shape.

6. A torque device for selectively gripping a guidewire, said torque device comprising:
   a housing defining a first portion of a lumen dimensioned to receive the guidewire, wherein a transverse cross-section of the first portion of the lumen is non-circular having a large area that tapers to a narrow area, and wherein a portion of said housing defines a stop;
   an actuator defining a second portion of said lumen and having a catch, wherein a transverse cross-section of the second portion of the lumen is non-circular having a large area that tapers to a narrow area, wherein the transverse cross-section of the second portion of the lumen has an inverted orientation relative to the transverse cross-section of the first portion of the lumen, and wherein said actuator is slidably mounted to permit linear translation motion within said housing; and
   a resilient member biasing said actuator from a first position in which the large area of the first portion of the lumen and the large area of the second portion of the lumen are aligned, toward a second position in which the large areas of the first and second portions of said lumen are misaligned and the narrow area of the first portion of the lumen engages two or more elongate areas of contact extending along a length of the surface of the guidewire and the narrow area of the second portion of the lumen engages two or more elongate areas extending along a length of the surface of the guidewire when the actuator is in the second position, wherein movement of said actuator in a direction of the bias is limited by interference of said catch with said stop.

7. The torque device of claim 6, wherein said lumen is substantially continuous through said housing and said actuator.

8. The torque device of claim 6, wherein said housing and said actuator are shaped to maintain said first and second portions of said lumen in substantial alignment in a longitudinal direction.

9. The torque device of claim 6, wherein said catch comprises a resilient catch that is configured to deflect as said actuator is inserted into said housing during assembly and configured to resile after said actuator is positioned in said housing.

10. The torque device of claim 6, wherein the first portion of said lumen is teardrop-shaped in cross-section.

11. A torque device for selectively gripping a guidewire, said torque device comprising:
   a housing defining a first portion of a lumen dimensioned to receive the guidewire, wherein a transverse cross-section of the first portion of the lumen is non-circular having a large area that tapers to a narrow area;
   an actuator defining a second portion of said lumen, wherein a transverse cross-section of the second portion of the lumen is non-circular having a large area that tapers to a narrow area, wherein the transverse cross-section of the second portion of the lumen has an inverted orientation relative to the transverse cross-section of the first portion of the lumen, and wherein said actuator is slidably mounted on said housing, and wherein said housing and said actuator are shaped to maintain respective axes of said first and second portions of said lumen in substantial alignment in a longitudinal direction; and
   a resilient member biasing said actuator from a first position in which the large area of the first portion of the lumen and the large area of the second portion of the lumen are aligned, toward a second position in which the large areas of the first and second portions of said lumen are misaligned and the narrow area of the first portion of the lumen engages two or more elongate areas of contact extending along a length of the surface of the guidewire and the narrow area of the second portion of the lumen engages two or more elongate areas extending along a length of the surface of the guidewire when the actuator is in the second position.

12. The torque device of claim 11, wherein said actuator is slidably mounted to permit linear translation motion within a channel defined by said housing, said actuator and said channel being oblong in transverse cross-section.

13. The torque device of claim 11, wherein said lumen is substantially continuous through said housing and said actuator.

14. The torque device of claim 11, wherein said housing comprises a plurality of ribs defining an outer grasping surface.

15. A torque device for selectively gripping a guidewire, said torque device comprising:

an elongated housing defining a longitudinally-extending lumen dimensioned to receive the guidewire, the housing having a proximal end defining a proximal portion of said lumen and a distal end defining a distal portion of said lumen that is longitudinally aligned with said proximal portion of said lumen, wherein a transverse cross-section of the proximal portion of the lumen and a transverse cross-section of the distal portion of the lumen are non-circular having a large area that tapers to a narrow area, said housing defining intermediate said proximal and distal ends a channel extending substantially perpendicularly to a direction of elongation of said lumen;

an actuator slidably mounted to permit linear translation motion within said channel, said actuator defining a longitudinally-extending actuator portion of said lumen, wherein a transverse cross-section of the actuator portion of the lumen is non-circular having a large area that tapers to a narrow area, wherein the transverse cross-section of the second portion of the lumen has an inverted orientation relative to the transverse cross-section of the first portion of the lumen, said actuator and said channel being oblong in transverse cross-section; and a resilient member biasing said actuator toward a position in which the large area of the actuator portion of said lumen is misaligned with the large areas of said proximal and distal portions of said lumen and the narrow area of the actuator portion of the lumen engages two or more elongate areas of contact extending along a length of the surface of the guidewire and the narrow areas of the proximal and distal portions of the lumen each engage two or more elongate areas extending along a length of the surface of the guidewire.

16. The torque device of claim 15, wherein said lumen is substantially continuous from said proximal portion, through said actuator portion, to said distal portion.

17. The torque device of claim 16, wherein a wall of said actuator portion of said lumen is cylindrical in shape.

18. The torque device of claim 15, wherein said housing defines an opening, and wherein said actuator comprises a resilient catch that is received in said opening and that interferes with said housing to retain said biased actuator within said channel.

19. The torque device of claim 15, wherein one of said proximal portion, said distal portion, and said actuator portion of said lumen is teardrop-shaped in cross-section.

20. The torque device of claim 15, wherein said resilient member comprises a coil spring.

21. The torque device of claim 20, wherein said actuator comprises a stop surface disposed to prevent actuator travel within said channel during depression of said actuator beyond a point at which said proximal and distal portions of said lumen are longitudinally aligned.

22. The torque device of claim 20, wherein said actuator comprises a post for supporting said coil spring.

23. The torque device of claim 22, wherein the body comprises a recess for maintaining the position of the coil spring relative to the body.

* * * * *